US009787833B2

(12) United States Patent
Omi et al.

(10) Patent No.: US 9,787,833 B2
(45) Date of Patent: Oct. 10, 2017

(54) NURSE CALL SYSTEM, NURSE CALL CONVERSION UNIT, NURSE CALL CONNECTION METHOD, AND PROGRAM

(71) Applicants: NEC Platforms, Ltd., Kawasaki-shi, Kanagawa (JP); NIPPON TELEGRAPH AND TELEPHONE EAST CORPORATION, Tokyo (JP); NIPPON TELEGRAPH AND TELEPHONE WEST CORPORATION, Osaka-shi, Osaka (JP)

(72) Inventors: Takuya Omi, Kanagawa (JP); Shigeru Maruyama, Kanagawa (JP); Kou Nogami, Tokyo (JP); Rintarou Ashida, Tokyo (JP); Ken Utsuki, Tokyo (JP); Norio Murakami, Osaka (JP)

(73) Assignees: NEC Platforms, Ltd., Kawasaki-shi (JP); NIPPON TELEGRAPH AND TELEPHONE EAST CORPORATION, Tokyo (JP); NIPPON TELEGRAPH AND TELEPHONE WEST CORPORATION, Osaka-shi (JP)

( * ) Notice: Subject to any disclaimer, the term of this patent is extended or adjusted under 35 U.S.C. 154(b) by 0 days.

(21) Appl. No.: 15/305,894

(22) PCT Filed: Oct. 22, 2015

(86) PCT No.: PCT/JP2015/079855
§ 371 (c)(1),
(2) Date: Oct. 21, 2016

(87) PCT Pub. No.: WO2016/072283
PCT Pub. Date: May 12, 2016

(65) Prior Publication Data
US 2017/0048389 A1 Feb. 16, 2017

(30) Foreign Application Priority Data
Nov. 7, 2014 (JP) .................................. 2014-226789

(51) Int. Cl.
H04M 3/46 (2006.01)
H04M 3/42 (2006.01)
(Continued)

(52) U.S. Cl.
CPC ............ *H04M 3/465* (2013.01); *A61G 12/00* (2013.01); *G08B 25/00* (2013.01);
(Continued)

(58) Field of Classification Search
CPC ............ G08B 25/00; H04M 9/00; H04Q 3/58
See application file for complete search history.

(56) References Cited

U.S. PATENT DOCUMENTS 5,563,940 A * 10/1996 Tsuzuki ............ H04M 3/42314
379/211.01
6,295,349 B1 * 9/2001 Nakamura ............. H04Q 3/625
370/522

FOREIGN PATENT DOCUMENTS

CN 2632967 Y 8/2004
CN 101014074 A 8/2007
(Continued)

OTHER PUBLICATIONS

Guidelines regarding connection between a nurse call or an interphone of an apartment house and a PBX, Sep. 25, 2002, 31 pages.
(Continued)

Primary Examiner — Harry S Hong
(74) Attorney, Agent, or Firm — Sughrue Mion, PLLC

(57) ABSTRACT

In nurse call systems that enable communication from a plurality of cordless handsets with a plurality of extension terminals carried by nurses belonging to a group, a nurse call
(Continued)

conversion unit is provided between a nurse call control device and a private branch exchange. A call signal for a group representative call in which only an identification number for a group is given is transmitted by the nurse call conversion unit from the nurse call control device to the private branch exchange. From this call signal, the private branch exchange generates a call signal for extension terminals belonging to a group and calls the extension terminals.

7 Claims, 6 Drawing Sheets

(51) Int. Cl.
| | |
|---|---|
| *A61G 12/00* | (2006.01) |
| *G08B 25/00* | (2006.01) |
| *H04M 9/00* | (2006.01) |
| *H04Q 3/58* | (2006.01) |
| *H04W 84/16* | (2009.01) |

(52) U.S. Cl.
CPC ......... *H04M 3/42314* (2013.01); *H04M 9/00* (2013.01); *H04Q 3/58* (2013.01); *H04W 84/16* (2013.01)

(56) References Cited

FOREIGN PATENT DOCUMENTS

| | | |
|---|---|---|
| JP | 2006-41831 A | 2/2006 |
| JP | 2006-186498 A | 7/2006 |
| JP | 2007-124312 A | 5/2007 |
| JP | 2010-57083 A | 3/2010 |

OTHER PUBLICATIONS

International Search Report for PCT/JP2015/079855 dated Dec. 22, 2015 [PCT/ISA/210].

Chinese Office Action; Application No. 201580020806; dated Aug. 7, 2017; NEC Platforms, Ltd.

\* cited by examiner

|  | PS-ID | Extension Number | Caller Number |
|---|---|---|---|
| Group Representative Number | 0110 | 110 | 0110 |
| PHS #1 | 0111 | 111 | 0111 |
| PHS #2 | 0112 | 112 | 0112 |
| PHS #3 | 0113 | 113 | 0113 |
| Group Representative Number | 0120 | 120 | 0120 |
| PHS #4 | 0121 | 121 | 0121 |
| ⋮ | ⋮ | ⋮ | ⋮ |

Fig.3

NURSE CALL SYSTEM, NURSE CALL CONVERSION UNIT, NURSE CALL CONNECTION METHOD, AND PROGRAM

CROSS REFERENCE TO RELATED APPLICATIONS

This is a U.S. national stage of application No. PCT/JP2015/079855, filed on Oct. 22, 2015. Priority under 35 U.S.C.§119(a) and 35 U.S.C.§365(b) is claimed from Japanese Patent Applications No. 2014-226789 filed on Nov. 7, 2014, the disclosure of which is also incorporated herein by reference.

TECHNICAL FIELD

The present invention relates to a nurse call system, a nurse call conversion unit, a nurse call connection method, and a computer program.

BACKGROUND ART

In a hospital, a nursing-and-caring facility, or the like, it may be installed a nurse call system which allows a patient and a nurse (a person to be cared and a care worker in a case of a nursing-and-caring facility or the like) to have a telephone conversation therebetween. Such a nurse call system is a system in which a nurse call apparatus and a private branch exchange (PBX, or a key telephone master unit) operate in association with each other, and a nurse call master unit accommodates nurse call slave units allocated to patients (or beds) in sickrooms, respectively. Also, each of nurses carries a portable terminal (such as a personal handy-phone system (PHS) terminal, a personal access system (PAS) terminal, and the like, which will hereinafter be referred to as a "PHS terminal"), and the portable terminal is configured so as to be accommodated in a private branch exchange via a radio line.

For a patient to summon a nurse, the patient makes a nurse call to an extension number of a PHS terminal from a nurse call slave unit, and the PHS terminal is called up from a nurse call master unit via a private branch exchange, to thereby have a telephone conversation. Conversely, also a PHS terminal can call up a nurse call slave unit of a patient, and have a telephone conversation. Further, in light of nursing in teams, PHS terminals carried by nurses are divided into some teams, and the system is configured such that PHS terminals of a plurality of nurses belonging to one team can be simultaneously called up from a slave unit, to thereby summon nurses who are in charge of a patient at one floor.

An example of the above-described nurse call system is shown in FIG. 5. The nurse call system includes a nurse call controller 20 which accommodates a plurality of nurse call slave units 10 (SU 11-1, 11-2, 11-3, 12-1, 12-2, 12-3, ... ), a private branch exchange (PBX) 40 which accommodates a plurality of PHS terminals 50 belonging to either of two groups (teams) (PHS terminals 51-1, 51-2, and 51-3 in a first group, and PHS terminals 52-1, 52-2, and 52-3 in a second group) via a radio line, and a nurse call adapter 32 which is interposed between the nurse call controller 20 and the private branch exchange 40 and converts an interface between the nurse call controller 20 and the private branch exchange 40. In this regard, the nurse call controller 20 is a representation of a part of functions which relates to control of communication or the like of a nurse call master unit accommodating the plurality of nurse call slave units 10, and forms a part of the nurse call master unit.

There will be described about connection of the nurse call controller 20 having the above-described structure, to the private branch exchange 40 via the nurse call adapter 32. In FIG. 6, for the sake of explanation, it is assumed that the nurse call slave units 10 include only a slave unit #1, a slave unit #2, a slave unit #3, and a slave unit #4, and that three PHS terminals PHS #1, PHS #2, and PHS #3 belong to one group (group #1) in the PHS terminal 50. Thus, PHS #4 belongs to another group. As shown in FIG. 6, the nurse call adapter 32 achieves connection by connecting the nurse call controller 20 to an analog line unit 43 accommodated in the private branch exchange 40. The nurse call adapter 32 relays two lines with four speech paths (channels) included in the nurse call controller 20 to eight analog lines with eight speech paths included in the analog line unit 43. That is, data channels of four channels of ISDN basic interface (2B+D)×2 of the nurse call controller 20 is converted into an analog line, to achieve connection to the analog line unit 43 of the private branch exchange 40.

As a result of this, as shown in FIG. 6, a channel #1 of the nurse call controller 20 is converted into an analog line with channels, the number of which correspond to the number of PHS terminals in the group #1, in the nurse call adapter 32, and the channels are contained in a channel #1, a channel #2, and a channel #3 of the analog line unit 43 of the private branch exchange 40, and connected to channels #1-3 of the private branch exchange 40, so that some (PHS #1 to PHS #3) of the PHS terminals 50, the number of which correspond to the number of extension terminals in the group #1 of the private branch exchange 40 can be called up.

CITATION LIST

Non Patent Literature

{NPL 1} Guidelines regarding connection between a nurse call or an inter-phone of an apartment house and a PBX, 25 Sep. 2002.

SUMMARY OF INVENTION

Technical Problem

However, a nurse call adapter is configured as an apparatus dedicated to a nurse call system, and is expensive, so that introduction thereof is difficult. For this reason, there is a demand for an apparatus alternative to a nurse call adapter. There is also a demand for techniques which allows a nurse call controller and a private branch exchange to be connected to each other without changing central processing units (CPU) of a nurse call controller and a private branch exchange, and without significantly changing software.

Further, in a case where a nurse call adapter is not used, in a call from the nurse call controller 20, a private branch exchange is notified of only one message including identification numbers of PHS terminals (PS-ID), the number of which correspond to the number of PHS terminals to be called up. Thus, calls to the respective PHS terminals cannot be distributed. Even if calls to the respective PHS terminals can be distributed, in order to call up PHS terminals of a private branch exchange, the number of which is eight at the maximum, the number of channels between a nurse call controller and a private branch exchange, which is predetermined to be four, is probably insufficient, so that speech paths cannot be efficiently used.

An object of the present invention is to provide a nurse call system, a nurse call connection method, and a computer program, which allow a speech path between a nurse call controller and a private branch exchange to be efficiently used without using a nurse call adapter, and without changing a conventional nurse call controller, and a control circuit and software of the private branch exchange.

Solution to Problem

To solve the above described problem, a first aspect of the present invention is a nurse call system comprising: a nurse call controller accommodating a plurality of slave units; and a private branch exchange accommodating a plurality of extension terminals, in which: the slave units and the extension terminals form speech paths, to thereby have telephone conversations therebetween; the plurality of extension terminals are divided into a plurality of groups each of which is allocated with a group identification number (ID); and if a call for extension terminals belonging to one of the groups is received from one of the slave units, the nurse call controller sends a call signal including a group identification number of the group concerned and identification numbers of the extension terminals belonging to that group; and the private branch exchange makes a call, for an incoming call signal assigning one of the groups, to all of extension terminals belonging to the assigned group; which is characterized in that: a nurse call conversion unit is provided between the nurse call controller and the private branch exchange, to receive a call signal including a group identification number and identification numbers of extension terminals belonging to the group concerned incoming from the nurse call controller, extract only the group identification number from the received call signal, and send it as a call signal assigning that group, to the private branch exchange.

Another aspect of the present invention is a nurse call conversion unit which is used in a nurse call system in which: the nurse call system comprising a nurse call controller accommodating a plurality of slave units, and a private branch exchange accommodating a plurality of extension terminals, wherein: the slave units and the extension terminals forming speech paths, to thereby have a telephone conversation therebetween; the plurality of extension terminals are divided into a plurality of groups each of which is allocated with a group identification number (ID); and if a call for extension terminals belonging to one of the groups is received from one of the slave units, the nurse call controller sends a call signal including a group identification number of the group concerned and identification numbers of the extension terminals belonging to that group; and the private branch exchange makes a call, for an incoming call signal assigning one of the groups, to all of extension terminals belonging to the assigned group, the nurse call conversion unit is characterized by: being provided between the nurse call controller and the private branch exchange to: receive a call signal including a group identification number and identification numbers of extension terminals belonging to the group concerned incoming from the nurse call controller, extract only the group identification number from the received call signal, and send it as a call signal assigning that group to the private branch exchange.

Another aspect of the present invention is a nurse call connection method with a nurse call controller accommodating a plurality of slave units, and a private branch exchange accommodating a plurality of extension terminals; in which: the slave units and the extension terminals forms speech paths, to thereby have a telephone conversation therebetween; the plurality of extension terminals are divided into a plurality of groups each of which is provided with a group identification number (ID); when a call for extension terminals belonging to one of the groups is received from one of the slave units, the nurse call controller sends a call signal including a group identification number of the group concerned and identification numbers of the extension terminals belonging to that group and when a call signal assigning one of the groups is received, the private branch exchange makes a call to all of extension terminals belonging to the assigned group; which is characterized in that: a nurse call conversion unit is provided between the nurse call controller and the private branch exchange, and the nurse call conversion unit receives a call signal including a group identification number and identification numbers of extension terminals belonging to the group concerned incoming from the nurse call controller, extracts only the group identification number from the received call signal, and sends it as a call signal assigning that group to the private branch exchange.

Additionally, an information processor may be used as a computer program which implements a function of a nurse call conversion unit.

Advantageous Effects of Invention

According to the present invention, between a nurse call controller and a private branch exchange, a representative identification number of a group is included in a call signal provided from the nurse call controller, and is transmitted as one call message, so that the private branch exchange can call to extension numbers of all extension terminals belonging to the group by direct inward dialing. This can improve efficiency in use of channels, and reduces a probability of falling short of channels in number in calling up all of extension terminals in a group.

BRIEF DESCRIPTION OF DRAWINGS

FIG. 3 is a view for describing allocation of group representative numbers and PHS terminals, according to the embodiment of the present invention.

DESCRIPTION OF EMBODIMENTS

Embodiments of the present invention will now be described with reference to the accompanying drawings.

Figure 1:
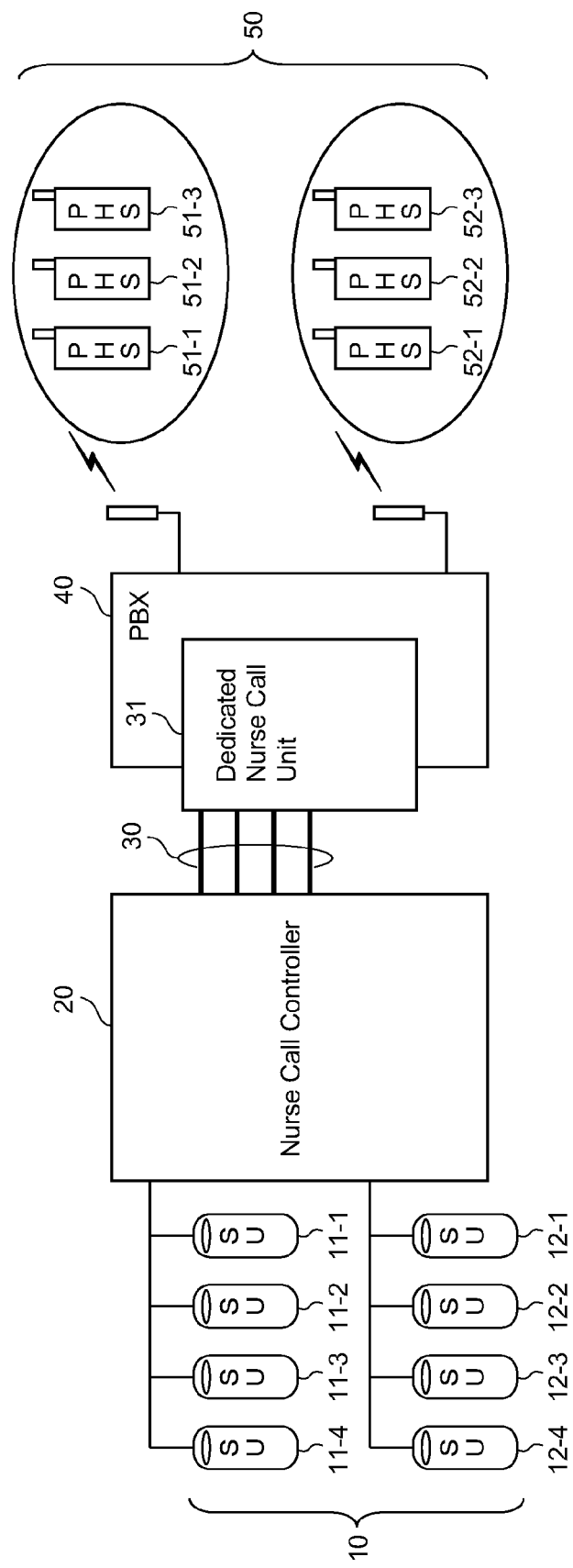
FIG. 1 is a view showing a configuration according to an embodiment of the present invention.

FIG. 1 shows a construction of a whole of a nurse call system according to an embodiment. The nurse call system according to the embodiment includes: a nurse call controller 20 which accommodates a plurality of nurse call slave units 10; a private branch exchange 40; a plurality of PHS terminals 50 which serve as extension terminals of the private branch exchange 40, are accommodated in the private branch exchange 40, and are carried by nurses (or care workers and the like); and a dedicated nurse call unit 30 which is located between the nurse call controller 20 and the private branch exchange 40 and notifies the private branch exchange 40 of an identification number of a PHS terminal (PS-ID) included in a call message, as a call message to which a group representative of a group identification number, is given. Meanwhile, the PHS terminals 50 are accommodated in the private branch exchange 40 as extension terminals, and are divided into groups of a first group including PHS 51-1, 51-2, 51-3, and 51-4, a second group including PHS 52-1, 52-2, 52-3, and 52-4. Also, as is appreciated from illustration of nurse call slave units 11-1 to 11-4, 12-1 to 12-4, many nurse call slave units 10 are accommodated in the nurse call controller 20, and are collectively denoted by a reference numeral "10".

Each of the nurse call slave units 10 is installed for a patient (or a bed), and includes various buttons and a call function, so that a nurse center or a nurse can be summoned by manipulating the buttons or the like. The nurse call controller 20 is a representation of a part relating to control in the nurse call master unit which accommodates the nurse call slave units, as described above, and has functions of controlling making of a nurse call, communication, and the like.

The private branch exchange 40 is configured to have a function of an exchange between extensions or between an exterior and an interior, and serves as a key telephone master unit. Also, the private branch exchange 40 accommodates the plurality of PHS terminals 50 which are portable terminals, via a radio line, and controls exchange in communicating with the PHS terminals 50. Further, the private branch exchange 40 is connected with the nurse call controller 20, and controls a call to the PHS terminals 50 with a nurse call, a call to the nurse call slave units 10 from the PHS terminals 50, and the like.

The dedicated nurse call unit 31 is interposed between the nurse call controller 20 and the private branch exchange 40, and converts a call message provided from the nurse call controller 20. Note that, though the dedicated nurse call unit 31 is provided in the private branch exchange 40 in FIG. 1, the position in which the dedicated nurse call unit 31 may be placed is not limited, if the dedicated nurse call unit 31 has a function of converting a message between the nurse call controller 20 and the private branch exchange 40.

Additionally, while the private branch exchange 40 can be connected to a plurality of nurse call controllers 20, an example in which the private branch exchange 40 is connected to one nurse call controller 20 is shown in FIG. 1, for the sake of explanation. Also, the number of the nurse call slave units 10 accommodated in one nurse call controller 20 (nurse call master unit), or the number of the PHS terminals 50 accommodated in the private branch exchange 40 depends on a specification of a nurse call system, and the number is not limited to any value.

Figure 4:
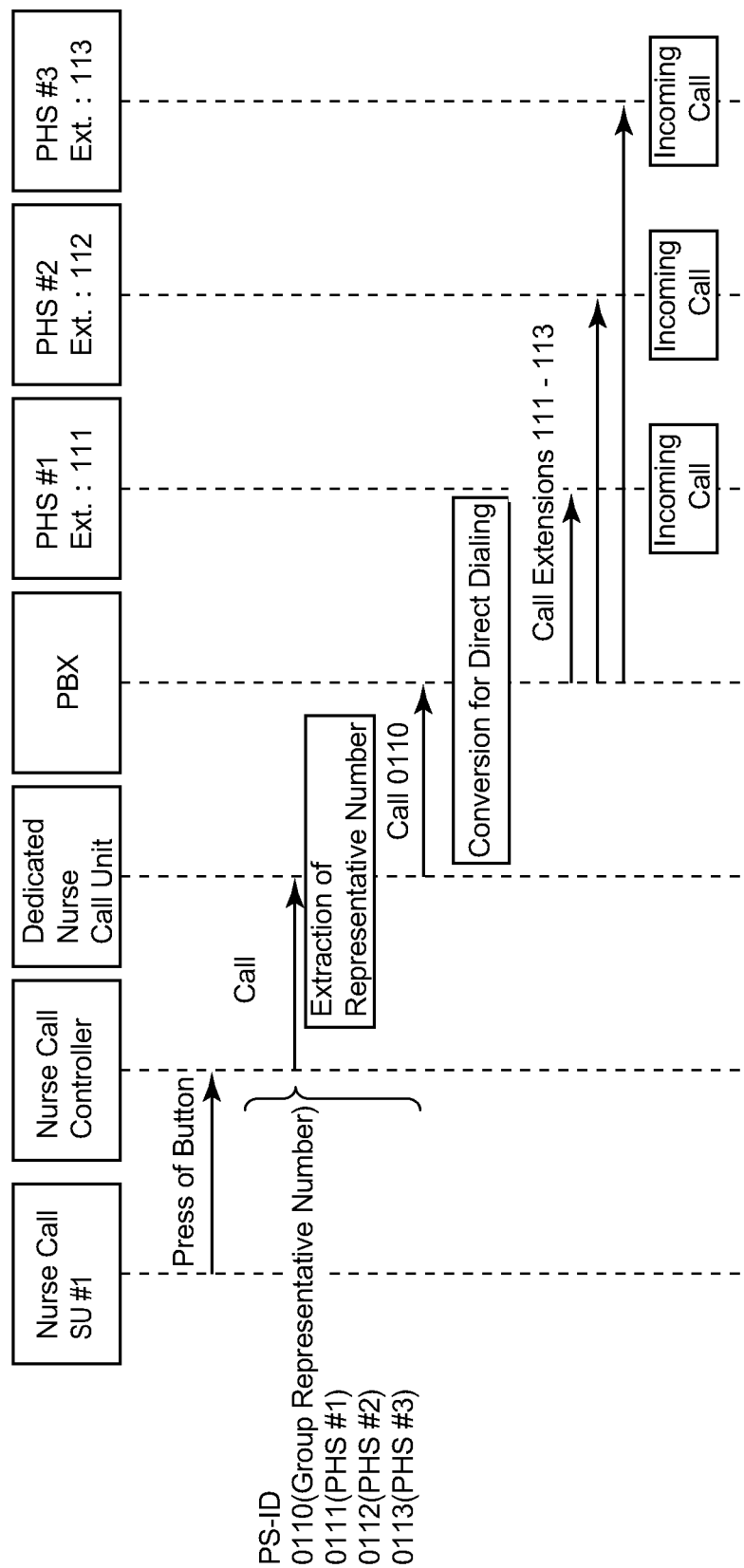
FIG. 4 is a sequence diagram for describing connection, according to the embodiment of the present invention.
Figure 5:
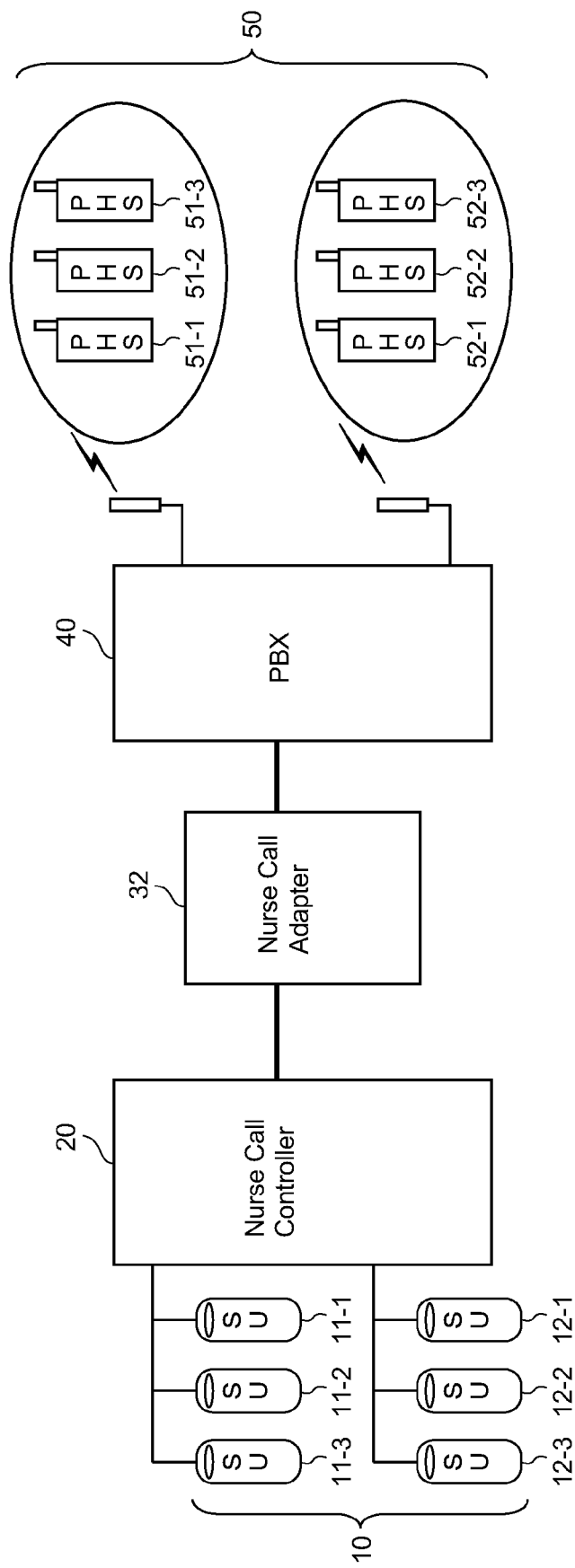
FIG. 5 is a view showing a nurse call system in which a conventional nurse call adapter is used.
Figure 6:
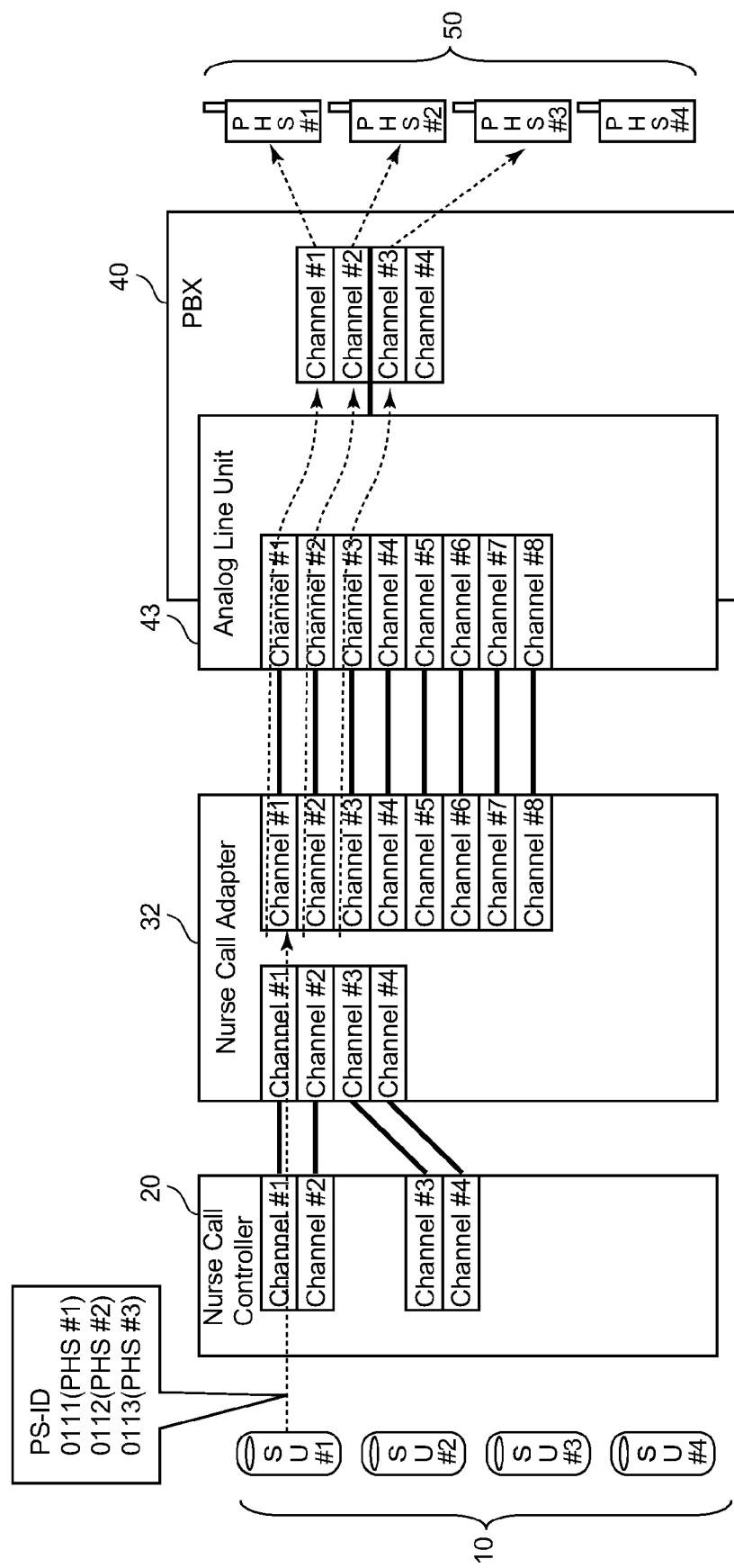
FIG. 6 is a view for describing connection in calling up a group according to conventional arts.

Next, with reference to FIGS. 2 to 4, a nurse call connection method in a call to a group with the use of a group representative number (group PS-ID) will be described.

Figure 2:
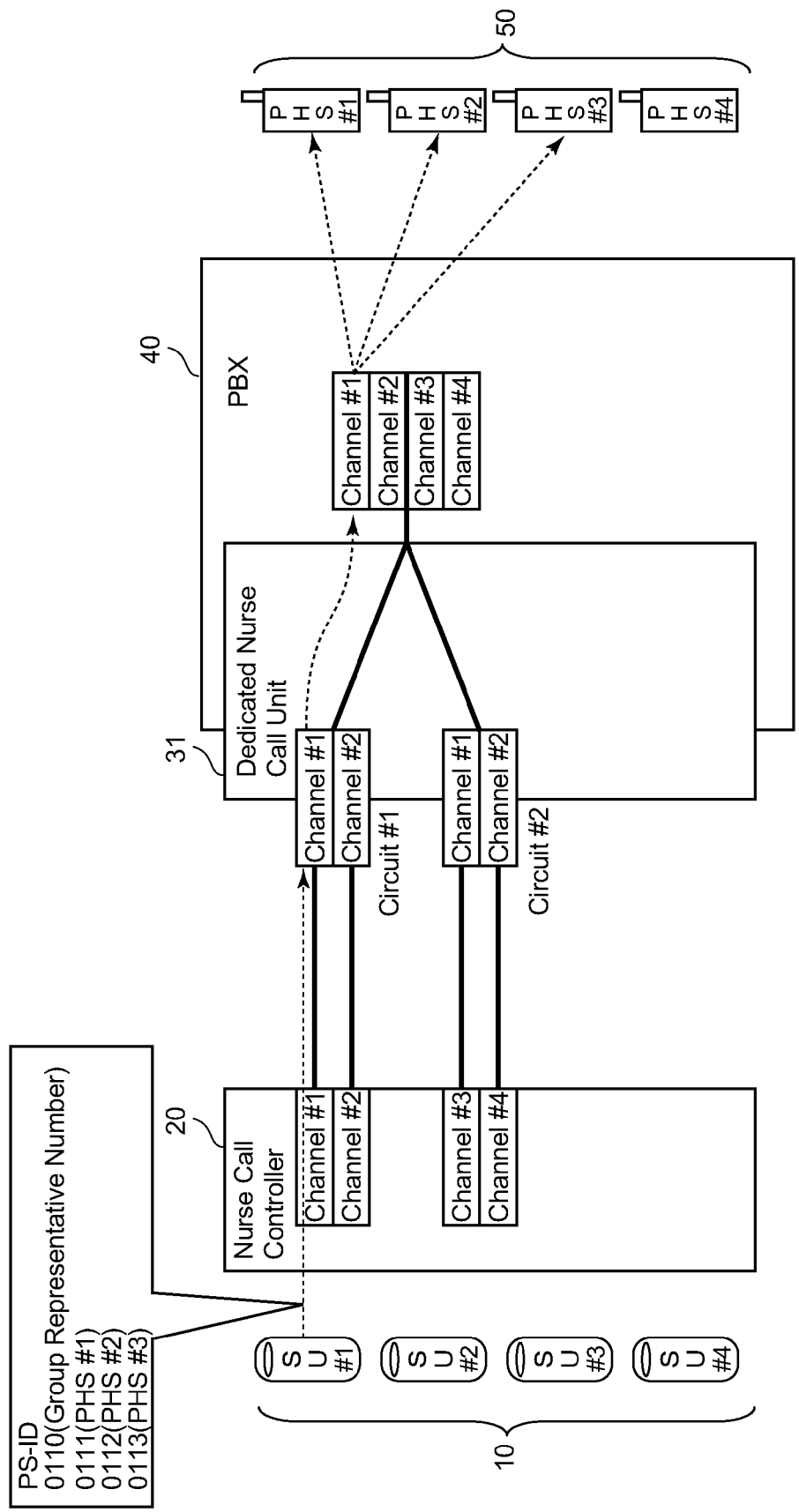
FIG. 2 is a view for describing connection in calling up a group with the use of a group representative number, according to the embodiment of the present invention.

FIG. 2 is a view for describing an example of connection achieved when the slave unit 1 of the nurse call slave units 10 calls three PHS terminals 50 (PHS1, PHS2, and PHS3) belonging to one group.

The nurse call controller 20 and the dedicated nurse call unit 31 are physically connected to each other by ISDN basic interface (2B+D)×2 via two lines with four speech paths. Also, the private branch exchange 40 accommodates four PHS terminals 50 in a communicatable state and are referred to as PHS #1 to PHS #4, respectively. Out of the four PHS terminals 50, the PHS #1 to PHS #3 are included in one group, and a number "0110" is given as a PS-ID of a group representative number for calling up the group.

A table in FIG. 3 shows allocation of group representative numbers and numbers of PHS terminals. A number "0110" is given as an identification number (PS-ID) of a representative number of a group to which the PHS #1 to PHS #3 belong, a number "0111" is given as an identification number PS-ID of the PHS #1, a number "111" is given as an extension number, and a number "0111" is given as a caller number. Likewise, a number "0112" is given as an identification number PS-ID of the PHS #2, a number "112" is given as an extension number, and a number "0112" is given as a caller number. A number "0113" is given as an identification number PS-ID of the PHS #3, a number "113" is given as an extension number, and a number "0113" is given as a caller number. That is, a number of which the least significant digit is zero and the other digit is equal to that of each of PS-IDs of PHS terminals belonging to a group which is to be called up is used as a group representative number. Additionally, since the PHS #4 belongs to another group, numbers "0120", "120", and "0120" are given as an identification number, an extension number, and a caller number, as a next PS-ID, or as a group representative number in a next group, and an identification number "0121", an extension number "121", and a caller number "0121" of the PHS #4 are given.

In the private branch exchange 40, direct inward dialing is set so that, in a case where there is an incoming call indicating a group representative number as an incoming call number, the PHS terminals 50 (PHS #1, PHS #2, and PHS #3) belonging to a PS-ID of the group representative number included in a call message can receive the incoming call. Also, when a PHS terminal responds to a call, the private branch exchange 40 notifies the nurse call controller 20 of a caller number of the PHS terminal.

The above-described table which shows PS-ID correspondences between group representative numbers and each of the PHS terminals is equipped in the dedicated nurse call unit 31 for converting a call message, and is referred to in converting a PS-ID of a call message provided from the nurse call controller 20. Also, a table including PS-IDs, extension numbers, and caller numbers is equipped in the private branch exchange 40, and is referred to in conversion into a number for direct inward dialing in response to a call to the PHS terminals 50, and in notification of a caller number when responding to a call. The table which shows correspondences between PS-IDs of group representative numbers and PS-IDs of PHS terminals is equipped also in the nurse call controller 20, and is referred to in notification of a call message in a case when there is a call to a group of PHS terminals from a nurse call slave unit.

Next, operations for a call to a PHS with the use of a group representative PS-ID will be described with reference to a sequence diagram therefore in FIG. 4.

A call button is pressed in the nurse call slave unit #1, and a call to a group is made. As a result of this operation for a call, the nurse call controller 20 notifies the private branch exchange 40 of the group representative number "0110" and identification numbers PS-IDs of the PHS terminals "0111", "0112", and "0113" which are associated with the PHS terminals belonging to the group, as one call message. The dedicated nurse call unit 31 analyzes the PS-IDs in the call message, and extracts the PS-ID of the group representative number "0110". Since the group representative number "0110" is a number the least significant digit of which is zero and the other digit of which is equal to that of each of the PS-IDs in group, when a PS-ID within the incoming call message is extracted from the higher significant digit, a group representative number PS-ID can be extracted first. Then, the extracted number is determined to be a group representative number, and the private branch exchange 40 can be notified of a call message to which the group representative number "0110" is given, with the use of one channel, without extracting any other PS-IDs of PHS terminals which have later numbers.

When the private branch exchange 40 is notified of a call message with a PS-ID of a group representative number, the private branch exchange 40 calls up extension numbers "111", "112", and "113" of PHS terminals by direct inward dialing in accordance with the group representative number. As a result of this, each of the PHS #1 to PHS #3 enters into a state where a call is incoming. If one of the PHS terminals responds to a call, the private branch exchange 40 notifies the nurse call controller 20 of a caller number of the PHS responding to the call. In the nurse call controller 20, a number (PS-ID) of the PHS responding to the call is recorded as a response history.

Additionally, a call signal provided from the nurse call controller 20 to the dedicated nurse call unit 31, can be also implemented by a signal in a form in which only a group representative number (PS-ID) is given and an identification number (PS-ID) of each of the PHS terminals 50 is not given.

The above-described operations for a call to a group with the use of a group representative number can be implemented as software which causes computers of the nurse call controller 20, the dedicated nurse call unit 31, and the private branch exchange 40 to operate. Particularly, in the dedicated nurse call unit 31, the operations can be implemented by using software which is designed to convert a group call signal to a call signal to which only a group representative number is given. Also, by utilizing an ISDN line unit which contains ISDN basic interface of the private branch exchange 40 for the dedicated nurse call unit 31, software for controlling conversion of an interface and conversion for direct inward dialing in a private branch exchange can be achieved.

As described above, a call to a group which is provided from the nurse call controller 20 to the private branch exchange 40 is conducted with the use of only one channel, so that it is possible to prevent as many channels as called terminals from being occupied in a call to a group, to thereby allow for efficient use of channels. Also, hardware and software should be changed only a little, to thereby reduce a cost.

The invention claimed is:

1. A nurse call system comprising:
a plurality of extension terminals grouped into a plurality of groups, each of the extension terminals being allocated with a terminal identification number (terminal ID) and each of the groups being allocated with a group identification number (group ID);
a private branch exchange configured to call extension terminals belonging to one of the groups in response to an incoming call signal assigning said one of the groups;
a plurality of slave units configured to perform telephone conversations with the extension terminals;
a nurse call controller configured to receive call requests from the slave units, at least one of the call requests requesting a call to extension terminals belonging to the one of the groups, and to send a call signal corresponding to the at least one of the call requests, the call signal comprising a group ID of the one of the groups and terminal IDs of the extension terminals belonging to the one of the groups; and
a nurse call conversion unit configured to provide an interface between the nurse call controller and the private branch exchange, wherein
the nurse call conversion unit is further configured to receive the call signal from the nurse call controller, to convert the call signal, into a second call signal by including the group ID into the second call signal and omitting the terminal IDs from the second call signal, and
the nurse call conversion unit is further configured to send the second call signal to the private branch exchange.

2. The nurse call system according to claim 1, wherein the nurse call conversion unit is further configured to convert the call signal to the second call signal by referencing a table describing correspondences between the group IDs, extension numbers and terminal IDs belonging to each of the groups.

3. A nurse call conversion unit comprising:
at least one hardware processor configured to implement:
interfacing a nurse call controller and a private branch exchange of a nurse call system;
receiving a call signal from a nurse call controller, the call signal comprising a group identification number (group ID) of a group of extension terminals and terminal identification numbers (terminal IDs) of the extension terminals;
converting the call signal into a second call signal by including the group ID into the second call signal and omitting the terminal IDs from the second call signal; and
sending the second call signal to the private branch exchange, wherein
the private branch exchange is configured to accommodate a plurality of extension terminals, comprising the extension terminals, grouped into a plurality of groups, comprising the group, each of the plurality of extension terminals being allocated with ones of terminal identification numbers (terminal ID), comprising the terminal IDs, and each of the groups being allocated with one of a plurality of group identification numbers (group IDs) comprising the group ID,
the private branch exchange is further configured to call the extension terminals corresponding to the group ID in response to the call signal,
the nurse call controller is configured to accommodate a plurality of slave units configured to perform telephone conversations with the extension terminals, and
the nurse call controller is further configured to receive call requests from the slave units, at least one of the call requests requesting a call to the extension terminals of the group, and to send the call signal.

4. The nurse call conversion unit according to claim 3, wherein:
the at least one hardware processor is further configured to implement:
converting the call signal to the second call signal by referencing a table describing correspondences between the group IDs, extension numbers and terminal IDs belonging to each of the groups.

5. A nurse call connection method comprising:
receiving, by a nurse call controller, a call request from a slave unit, the call request requesting a call to a group of extension terminals;

sending, by the nurse call controller, a call signal comprising a group identification number (group ID) of the group and terminal identification numbers (terminal IDs) of the extension terminals of the group;

receiving, by a nurse call conversion unit providing an interface between the nurse call controller and a private branch exchange, the call signal from the nurse call controller;

converting, by the nurse call conversion unit, the call signal into a second call signal by including the group ID into the second call signal and omitting the terminal IDS from the second call signal;

sending, by the nurse call conversion unit, the second call signal to the private branch exchange; and calling, by the private branch exchange, the extension terminals of the group in response to receiving the second call signal.

6. The nurse call connection method according to claim 5, wherein the nurse call conversion unit is further configured to convert the call signal into the second call signal by referencing a table describing correspondences between the group IDs, extension numbers and terminal IDs belonging to each of the groups.

7. A non-transitory computer-readable storage medium storing a computer program which is installed on an information processor, and configured to cause the information processor to implement a function corresponding to the nurse call conversion unit according to claim 3.

* * * * *